United States Patent [19]

Pettersson

[11] Patent Number: 5,676,154
[45] Date of Patent: Oct. 14, 1997

[54] BREATHING SENSOR DETECTING BREATH CONDENSATION

[75] Inventor: Hans Pettersson, Linghem, Sweden

[73] Assignee: Optovent AB, Sundbyberg, Sweden

[21] Appl. No.: 492,001

[22] PCT Filed: Jan. 19, 1994

[86] PCT No.: PCT/SE94/00037

§ 371 Date: Sep. 21, 1995

§ 102(e) Date: Sep. 21, 1995

[87] PCT Pub. No.: WO94/16620

PCT Pub. Date: Aug. 4, 1994

[30] Foreign Application Priority Data

Jan. 19, 1993 [SE] Sweden ............................... 9300137

[51] Int. Cl.⁶ .................................................. A61B 5/00
[52] U.S. Cl. ............................ 128/719; 128/716; 128/725; 73/355.01
[58] Field of Search ................................ 128/716, 719, 128/718, 725, 201.13; 607/88, 89; 73/23.2, 23.3, 29.01, 25.04, 335.01, 335.02; 422/83, 84, 98

[56] References Cited

U.S. PATENT DOCUMENTS

| 3,863,502 | 2/1975 | Elliot | 73/335.01 |
| 4,166,891 | 9/1979 | Elliot | 73/335.01 |
| 4,370,986 | 2/1983 | Gebhart et al. | 128/716 |
| 4,641,524 | 2/1987 | Tarvin | 73/335.01 |
| 5,319,975 | 6/1994 | Pederson et al. | 73/335.01 |
| 5,440,927 | 8/1995 | Chu et al. | 73/335.01 |

*Primary Examiner*—Lee S. Cohen
*Assistant Examiner*—Stephen Huang

[57] ABSTRACT

A method, a device and a sensor to sense the breathing of a man or an animal. A breathing sensor which, in an optical way, detects changes in deposited moisture on a sensor portion is placed in the breathing air flow, and changes of a transmitted or reflected optical signal dependent on deposited moisture is sensed as a measure of the breathing. A sensor according to the invention may consist of an optical fiber, one end surface of which constitutes a sensor surface and reflects a signal in the fiber to a varying degree dependent on mist deposited by the breathing air flow on the sensor surface. The sensor can be used in other environments as well, to detect a condensable vapor in a gas.

30 Claims, 4 Drawing Sheets

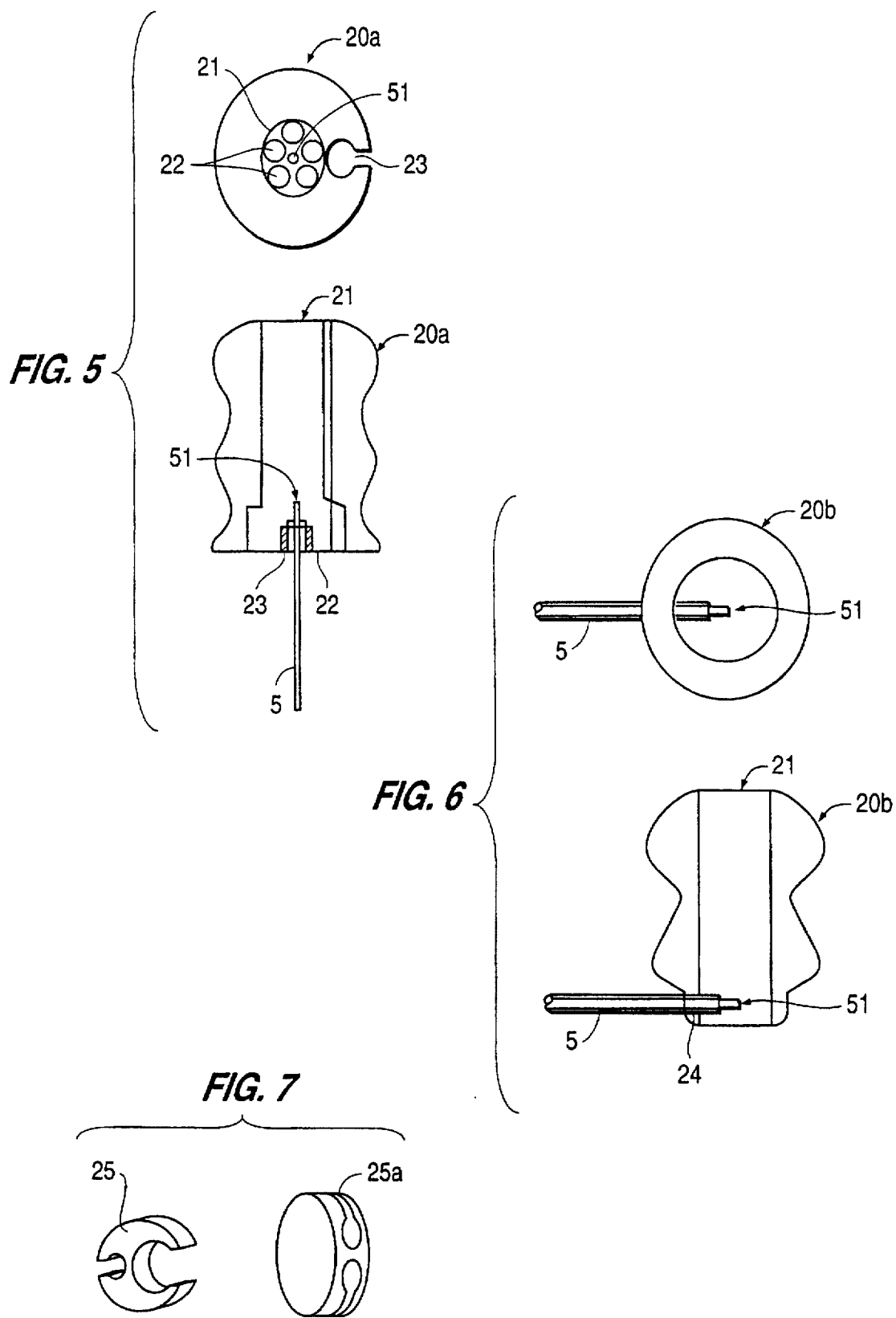

BREATHING SENSOR DETECTING BREATH CONDENSATION

The present invention refers to a method to sense the breathing of a man or an animal, a breathing sensor adapted to perform the method and a device to sense the breathing of a human or an animal.

SUMMARY OF THE INVENTION

The expression "to sense the breathing" in this document is referred primarily to achieve a signal which to a substantial extent follows the breathing air flow.

In many different situations there may be a reason to sense the breathing of a man or an animal. Various states of illness, intensive care, examinations of performances and breathing supervision during sleep are examples of such occasions when one wishes to measure the breathing rate and an eventual disruption of the breathing or study a wave shape corresponding to the breathing.

Many different methods have been tried to sense the breathing. Examples of such are those which are based on pressure changes in the breathing air flow that for example may influence a membrane, the curve of which is sensed by a strain gauge transducer or by another method. Another method is to let a thermistor be cooled by the breathing air flow and to sense the voltage level across the same, and an additional method is to sense the movement of a ball in the air flow.

An object of the present invention is to achieve a method and a device to sense the breathing and a breathing sensor of a new, simple and reliable type which can be utilized in a flexible way when there is desire to sense the breathing. An object is also to achieve breathing sensors which easily can be carried by a patient and which do not need to incorporate electric cables at the proximity of the body. An additional object is to achieve breathing sensors which are easy to keep clean and when needed sterile and which are so cheap that if desired they can be utilized as disposable products. Further objects and purposes appear in greater detail in connection with the following specification.

The method and the device to sense the breathing and the breathing sensor according to the present invention is based on the fact that the humidity of the breathing air varies strongly between in- and exhalation. At inhalation the relative humidity in the breathing air flow at the nose or the mouth approximately is the same as that of the ambient air, i.e. frequently far below 100% while at exhalation it is basically saturated with water vapour, i.e. 100% relative humidity.

If one allows the breathing air to pass a surface that is colder than 37° C. water will condense on the surface when expiration air passes. Mist is formed on the surface. If, for example, said surface constitutes the end of an optical fibre, the condensation course can be studied in the following way. Light or other electromagnetic beam is guided into the optical fibre which beam in turn can be guided by means of an optical fibre from a source which can be a laser, laser diode, light emitting diode or some other light bulb. The optical beam that reaches at the far end of the fibre partly will be reflected and partly leak out. If the end of the fibre becomes coated by mist tis relation will be changed so that a smaller part of the ray will be reflected back when the fibre is moist than when it is dry. The reason for this is that the small drops of water constituting the mist form small lenses which let out radiation in more angles than what is the case of the dry fibre. The breathing then can be sensed as intensity variations of the reflected light by any appropriate method which is exemplified below.

It is also possible to detect the intensity variations of the beam that is transmitted in order to sense the breathing from this variation. This can for example be carried out by means of a photo detector or another fibre end which captures a part of the transmitted radiation at the proximity of the first end of the fibre. It is also possible to use the principle according to the present invention in another way. For example a loop of an optical fibre can be utilized, where the sensor surface is constituted by a window of arbitrary form which lets out a part of the radiation guided in the fibre but guides the remainder further to the other end of the fibre. In the same manner as in the basic design the moisture on the window influences the intensity of the beam that is emitted through the window and thereby also the beam that is guided further in the fibre.

It is also possible to use the principle according to the invention without any optical conductor or fibre being used. If a wholly or partly reflective or transmitting element is placed in the breathing stream and exposed to an optical signal the transmitted or the reflected signal can be sensed and the breathing be determined from its variations. The optical signal can be directed directly against the reflective or transmitting element and the sensor likewise, or else either the source of the optical signal or the sensor or both may include reflective or transmitting elements which constitute a sensor surface.

Experiments which have been carried out with a reflected beam from a plastic optical fibre end, show that the intensity of the beam varies in good accordance with the breathing air flow and that no particular actions need to be carried out in order to lead off heat from the fibre end.

BRIEF DESCRIPTION OF THE DRAWINGS

The invention now will be described in closer detail in connection to the drawing, in which FIG. 1 diagrammatically shows a device according to the invention FIGS. 5 and 6 show further embodiments of breathing sensors according to the invention, and FIG. 7 shows a holder for an optical fibre and an oxygen catheter.

PREFERRED EMBODIMENTS OF THE INVENTION

Figure 1:
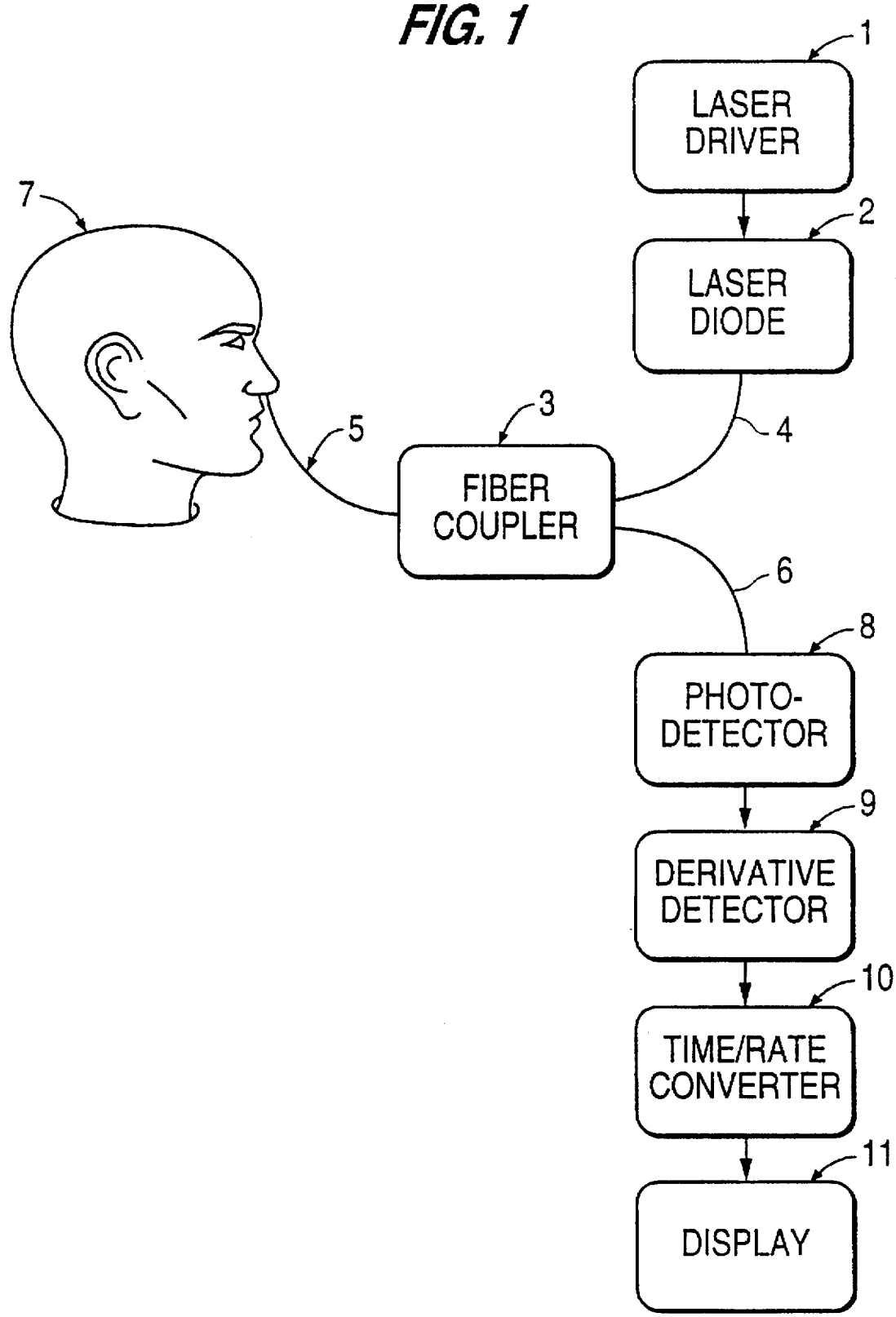

In the embodiment of the invention according to FIG. 1 a laser drive circuit 1 is coupled to a laser diode 2, the optical signal of which is conducted via a first optical conductor 4, a fibre coupler 3 and a second optical conductor 5 to the proximity of a breathing path of a person 7 who constitutes a measuring object. The fibre coupler 3 is such that the optical signal from the conductor 4 in the main is conducted further to the conductor 5 while the output signal on the third optical conductor 6 primarily originates from the optical signal which is conducted in the fibre coupler 3 from the other optical conductor 5 and which in the present case originates from the part of the signal from the laser diode 2 that is reflected by the end of the second optical fibre 5 where the very sensor surface is situated. The fibre coupler 3 can include the first (4) and the third (6) fibre being joined edge to edge with the second fibre 5, the diameter of which is twice the size of the rest.

From the third fire 6 the optical signal goes to a photo detector 8. The electric output signal which is generated by the light falling on the photo detector consists of two parts. A DC-level which only depends on the characteristics of the beam source, of the fibre and of the photo detector and a voltage variation superimposed on this which depends on how large a portion of the incident beam which, due to the mist on the sensor surface by the fibre end, is coupled out from the fibre at the measuring object. The superimposed voltage level has the character of a sinusoidal wave.

The breathing depending output signal from the photo detector 8 can be used and processed in various ways. What is illustrated in FIG. 1 is a detector circuit 9, which is intended to convert the signal of the photo detector to square wave pulses in time to the breathing. These are converted in the time-to-frequency converter 10 to the breathing frequency which is shown on a display 11.

Figure 2:
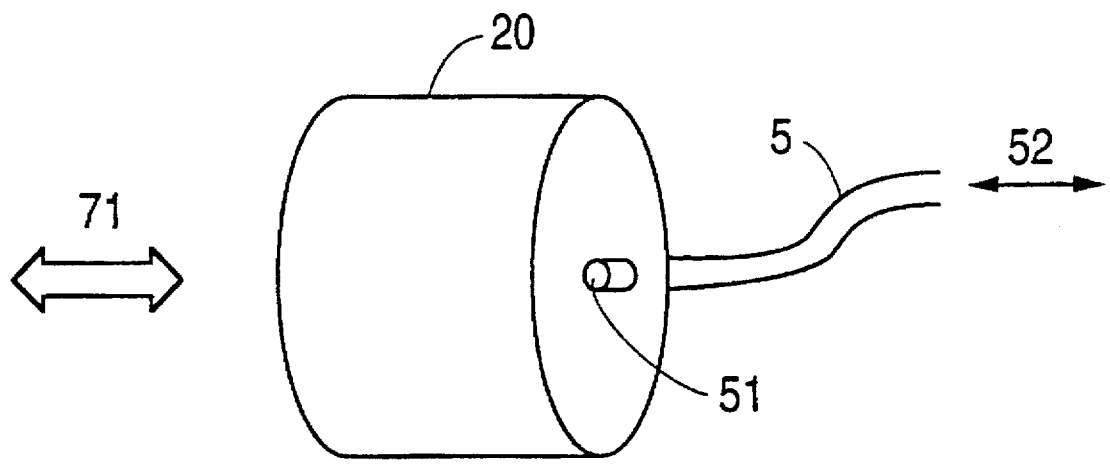
FIGS. 2 and 3 show different embodiments of breathing sensors according to the invention.

FIG. 2 shows a preferred embodiment of a breathing sensor according to the invention. The end surface 51 of the optical conductor 5 forms a sensor surface that normally lets out a part of the supplied optical signal and reflects a part, whereby the relationship between transmission and reflection is influenced by the condensation rate of the sensor surface 51 initiated by the air flow 71 of the breathing. The signal 52 in the optical conductor 5 consequently includes a supplied signal and a reflected signal. The end of the optical conductor 5 with the sensor surface 51 is surrounded by mainly a tubular holder 20 intended to keep the conductor 5 and the sensor surface 51 on site in the breathing air flow in for example a nostril. The optical conductor 5 can be constituted by a commercially available optical fibre of plastic. The sensor surface 51 preferably should lie mainly in parallel to the air flow.

Figure 3:
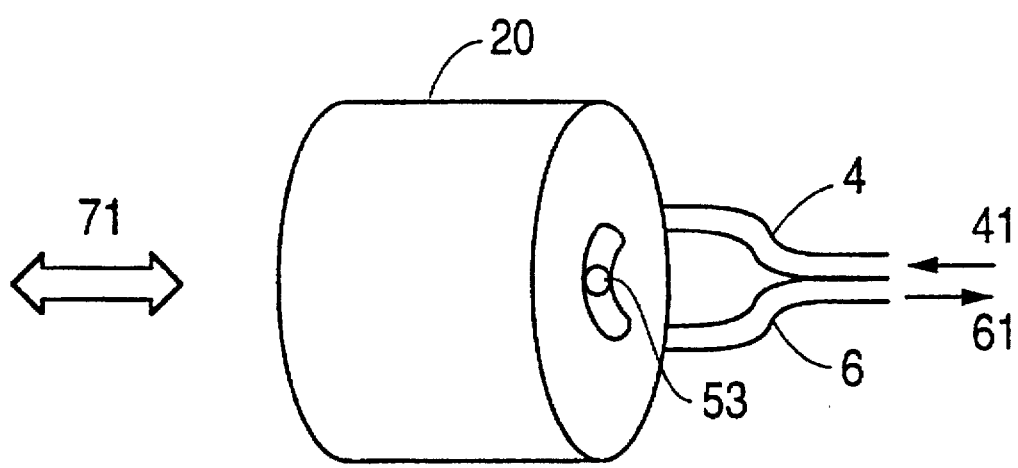

A variant of the breathing sensor appears in FIG. 3. The sensor surface 53 here instead constitutes a portion of an optical conductor on which the cladding layer of the conductor has been removed, and the conductor here instead constitutes a loop so that part of the beam supplied which does not leave the conductor at the sensor surface 53 is conducted further to a receiver. With this sensor no fibre coupler 3 or the like is required but one end 4 may receive the supplied beam 41 while the other end 6 emits an output signal 61 which can pass directly to a photo detector 8.

FIGS. 5 and 6 shows two alternate designs of the breathing sensors operating according to the same principle as that of FIG. 2. Both are built up from essentially tube shaped holders 20a and 20b respectively with a substantially ball shaped end intended to be inserted into the nose and possibly one or more external grooves, and contains a main channel 21 for the breathing stream. In the embodiment according to FIG. 5 the optical fibre 5 is fixed coaxially with the main channel 21 so that the sensor surface 51 is directed towards the breathing stream. A number of smaller holes 22 are arranged about the attachment for the optical fibre 5, so that the breathing stream can flow through the main channel 21, past the sensor surface 51 and through the holes 22. At a preferred embodiment the main channel 21 has a diameter reaching to about 8 mm which ends in five holes 22 of about 3.5 mm in diameter. A groove 23 for an oxygen catheter may be provided in the holder 20a, and an oxygen catheter may be guided together with the optical fibre 5 from the patient. Holder elements 25 or 25a according to FIG. 7, which have openings and channels adapted to retain the optical fibre and the oxygen catheter respectively, can be utilized for this purpose. At the second embodiment according to FIG. 6 the main channel 21 is passing through and the optical fibre 5 is provided radially in the main channel so that the breathing stream sweeps past and mainly parallel to the sensor surface 51. It is also possible to provide the fibre 5 and the sensor surface 51 in other angles with respect to the breathing stream than those appearing in the embodiments shown. The holders 20a and 20b are preferably made in plastic material, for example polyethene and the fibre 5 can be held on site in the holder by the fibre with its envelope being screwed into threaded holes 23 and 24 respectively in the holder.

As mentioned earlier even other designs of breathing sensor are conceivable and the patent protection should only be limited by the wording and equivalents of the patent claims. Within the scope of the inventive concept it is also possible for example to replace the tubular holder 20 with any other appropriate means for keeping the sensor surface in the breathing stream, such as a tape or the like or a holder designed otherwise. As an example the tubular holder 20 may be provided with a flap that facilitates tape fixation. Also, it is of course possible to provide sensors according to the invention in the breathing air flow to masks or tubes at respirators or other similar equipment.

A special application in which the invention can be of great value is the use in magnetic cameras. In these no metallic parts may be inserted and sick patients have to be monitored during relatively long examination times.

Figure 4:
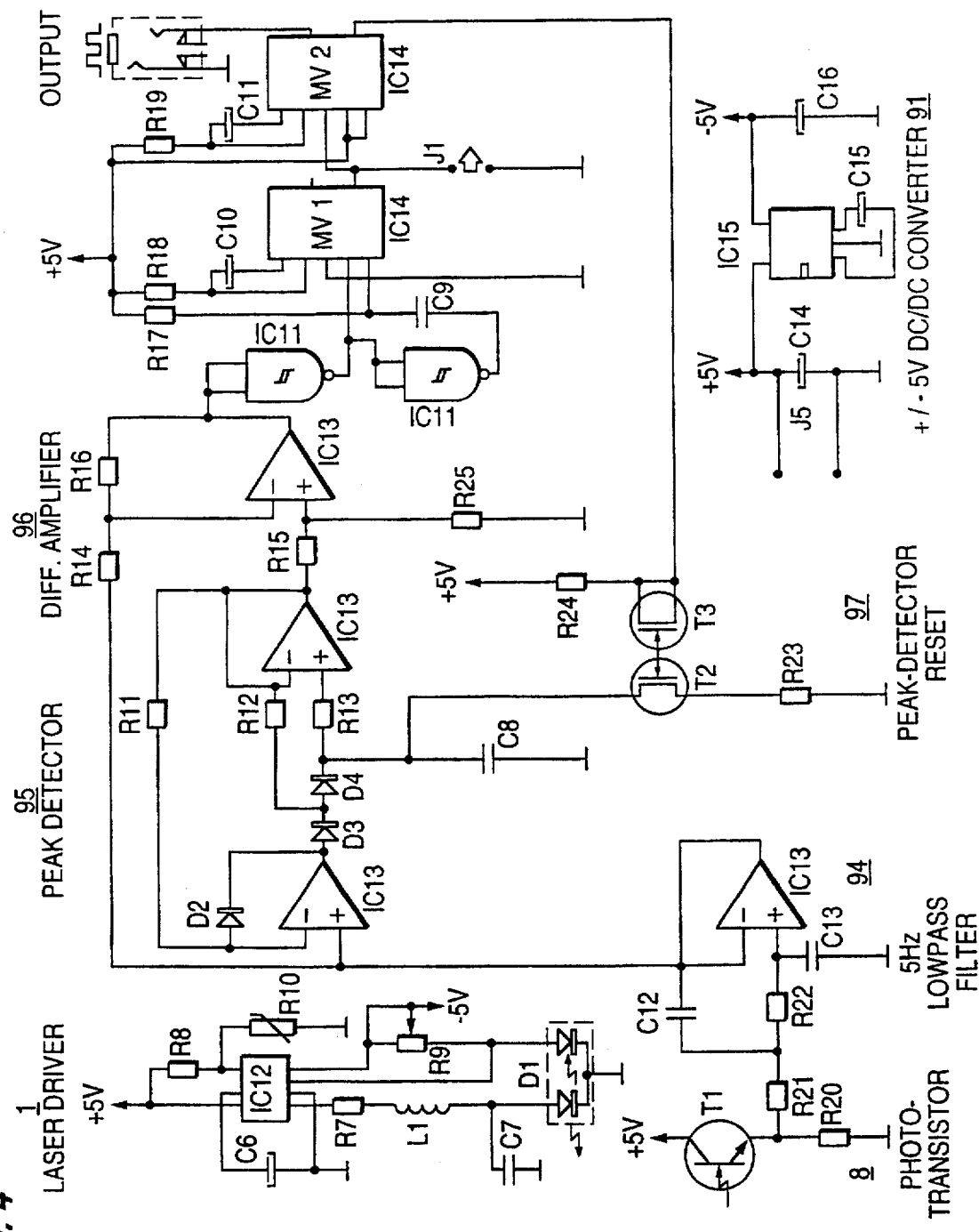
FIG. 4 shows an example of a circuit diagram which can be utilized at devices according to the invention.

An embodiment of the detector circuit 9 is shown in FIG. 4. This circuit has been designed to ensure the function of the breathing detector even by unsymmetrical and strongly disturbed breathing cycles. In addition to the main circuit for detection of the breathing signal FIG. 4 contains a ±5 volts converter circuit 91 and a drive circuit 1 for the laser diode D1.

The signal received by the photo transistor T1 (corresponding to designation no. 8 in FIG. 1) is brought to a low pass filter 94 with the cutoff frequency 5 Hz. The filtered signal is coupled to a peak-detector 95 built up of two operational amplifiers. In a differential amplifier 96 the difference is then formed between the signal son the peak-detector in- and outputs. At the output thereof now is found the upper peak value of the signal as a base line and the signal, amplified about 100 times, located on top of this line. The amplifier stage is followed by a pulse shaper consisting of two successive NAND-gates (IC 11). From the first NAND-gate a monostable multivibrator MV 1 is triggered with the pulse length of 6 seconds. This mono flip-flop only triggers on positive (=ascendant) pulse flanks. Next NAND-gate is coupled via a derivating net to the reset input of the mono flip-flop. The result will be that the 6-second pulse of the mono flip-flop is interrupted when the signal goes down which occurs by exhalation. If however, the expiration signal fails because of interference, or arrives too late, the time of 6 seconds will run out and the mono flip-flop resets. After the mono flip-flop MV 1 an additional mono flip-flop MV 2 of the pulse length 0.1 seconds follows, the mission of which is to reset the peak-detector 95 via two field effect transistors 97 so that a new inhalation phase can be started.

The output signal from the circuit is constituted by 0.1 second long pulses of time intervals that constitutes a measure of the breathing rate. The output signal can be connected to a frequency counter for conversion to a breathing rate after an appropriate number of pulses according to conventional technique. It can also be used directly to control an acoustic signal or presented on a display, which also can be done with the analogue breathing signal, which in that case suitably is extracted after the differential amplifier 96.

The circuit according to FIG. 4 is adapted to a detector according to FIG. 2, in which reflected light from the sensor surface is detected. If instead transmitted light from the sensor according to FIG. 3 is detected, the same circuit can be used on condition that the signal is inverted.

Component list to FIG. 4.

| Des. | Type/Value |
| --- | --- |
| IC11 | 4093 |
| IC12 | IR 3C02 |
| IC13 | TLC 274 |
| IC14 | 4538 |
| IC15 | 7660 |
| T1 | TEYT5500 |
| T2, T3 | 2N3820 |
| R7 | 22 Ω |
| R8 | 1.5 kΩ |
| R9 | 5 kΩ |
| R10 | 2.7 kΩ/20° C. |
| R11 | 20 kΩ |
| R12 | 1 MΩ |
| R13 | 10 kΩ |
| R14, R15 | 1 kΩ |
| R16, R17, R19 | 100 kΩ |
| R18 | 1.2 MΩ |
| R20 | 4.7 kΩ |
| R21 | 27 kΩ |
| R23 | 10 kΩ |
| R22, R24, R25 | 100 kΩ |
| C6 | 22 µF |
| C7 | 0.47 µF |
| C8, C9 | 100 nF |
| C10 | 4.7 µF |
| C11 | 1 µF |
| C12 | 0.68 µF |
| C13 | 0.33 µF |
| C14, C15, C16 | 10 µF |
| L1 | 47 µM |
| D1 | LT022MC |
| D2, D3, D4 | 1N4148 |
| D5 | 1N4004 |

I claim:

1. A method of sensing breathing of a man or an animal, comprising the steps of:

providing an optical breathing sensor in a breathing air flow of the man or animal; and, detecting changes in moisture deposited on the sensor, the moisture originating from the breathing air flow and causing optically detectable changes in transmitted and/or reflected optical signals in the breathing sensor.

2. The method according to claim 1, further comprising the steps of:

providing an optical conductor as the breathing sensor;

transmitting an optical signal into the optical conductor, an end surface of the conductor constituting a sensor surface of the breathing sensor and reflecting at least a portion of the optical signal back into the optical conductor; whereby changes in the optical signal reflection from the end surface are sensed in said detecting step, and the breathing is a function of the changes.

3. The method according to claim 1, further comprising the steps of:

providing an optical conductor as the breathing sensor;

transmitting an optical signal into the optical conductor, a portion of the conductor surface forming a window which constitutes a sensor surface of the breathing sensor, the moisture deposited on the window causing changes in the optical signal transmitted through the conductor past the window, the changes being sensed in said detecting step, and the breathing being a function of the changes.

4. The method of claim 1, wherein the deposited moisture is condensation from an exhale.

5. The method according to claim 1, wherein said step of providing includes the sub-steps of:

providing a holder for holding the breathing sensor inside an air flow passage of the man or animal; and inserting the holder into the air flow passage.

6. A breathing sensor, comprising:

a sensor surface for exposure to a breathing air flow;

an optical signal transmitted to said sensor surface; and a detecting circuit for detecting changes in the optical signal transmitted past or reflected by said sensor due to moisture from the air flow deposited on said sensor surface, the detected changes in the optical signal being a measure of the breathing air flow.

7. The breathing sensor according to claim 6, wherein said sensor surface is an end surface of an optical conductor, said optical conductor receiving said transmitted optical signal and conducting said optical signal to said sensor surface, the changes detected by said detecting circuit being changes in the optical signal reflected from the end surface back into said optical conductor.

8. The breathing sensor according to claim 7, wherein the end surface is arranged essentially perpendicular to said optical conductor.

9. The breathing sensor according to claim 7, wherein said sensor surface is arranged to be parallel to the breathing air flow.

10. The breathing sensor according to claim 7, wherein the sensor surface is provided essentially perpendicular to the breathing air flow.

11. The breathing sensor according to claim 6, further comprising:

an optical conductor having a window and receiving the transmitted optical signal, the optical signal being conducted to said window, said window constituting said sensor surface, the changes detected by said detecting circuit being changes in the optical signal transmitted through said optical conductor and past said window.

12. The breathing sensor according to claim 11, wherein the window is provided on a side surface of a loop formed by said conductor, the window essentially touching upon the breathing air flow.

13. The breathing sensor according to claim 6, wherein the deposited moisture is condensation from an exhaled air flow.

14. A device for sensing breathing of a man or an animal, comprising:

an optical source for emitting an optical signal;

a breathing sensor having a sensor surface to be placed in a breathing air flow of the man or animal, the optical signal reaching the sensor surface; and a detector for detecting changes in optical transmissivity and/or reflectivity of the sensor surface caused by variations in humidity deposited on the sensor surface from the breathing air flow, the detected changes indicating a measure of the breathing.

15. The device according to claim 14, said detector detecting changes in the optical signal transmitted past or reflected back from the sensor surface, said detector including means for sensing extreme values in the detected optical signal and for determining a breathing rate after a predetermined number of sensed extreme values.

16. The device according to claim 15, further comprising:

means for emitting an alarm of a ceasing breath a predetermined time period after an extreme value of the optical signal reaches and is detected by said detector, if no new extreme value before then is reached.

17. The device according to claim 14, further comprising:

means for emitting an alarm of a ceasing breath a predetermined time period after an extreme value of the optical signal has been sensed, if no new extreme value before then is reached.

18. The device according to claim 14, further comprising:

holding means for holding the sensor surface in a nostril of the man or animal.

19. The device according to claim 18, wherein said holding means further includes a catheter holder for holding a catheter in the nostril.

20. The device according to claim 14, wherein said breathing sensor includes an optical fiber, the sensor surface being a part of said optical fiber, said device further comprising:

holding means for holding the optical fiber in a nostril of the man or animal, said holding means being generally cylindrical with a central axis, the optical fiber being positioned generally along the central axis.

21. A method of sensing a condensable vapor in a gas, comprising the steps of:

providing an optical conductor having a sensing surface;

exposing the sensing surface to the gas;

transmitting an optical signal into the optical conductor, the sensing surface of the optical conductor reflecting at least a portion of the optical signal back into the optical conductor;

detecting changes in the optical signal reflected from the sensing surface, the changes corresponding to condensable vapor in the gas; and wherein the condensable vapor in the gas condenses on the sensing surface of the optical conductor thereby causing changes in the reflected optical signal.

22. The method of claim 21, wherein the gas moves intermittently such that said detecting step detects changes in condensation on the sensing surface caused by the intermittent movement of the gas.

23. The method of claim 21, wherein the sensing surface is an end surface of the optical conductor.

24. The method of claim 21, wherein the optical conductor is an optical fiber, the sensing surface being a side surface of the optical fiber.

25. The method of claim 21, wherein the gas is a man or animal's breath.

26. An apparatus for sensing a condensable vapor in a gas, comprising:

an optical conductor having a sensing surface, the sensing surface adapted to be exposed to a gas;

an optical signal source for transmitting an optical signal into the optical conductor, the sensing surface of the optical conductor reflecting at least a portion of the optical signal back into the optical conductor;

a detector for detecting changes in the optical signal reflected from the sensing surface, the changes corresponding to condensable vapor in the gas; and wherein the condensable vapor in the gas condenses on the sensing surface of said optical conductor thereby causing changes in the reflected optical signal.

27. The apparatus of claim 26, wherein the gas moves intermittently such that said detector detects changes in condensation on the sensing surface caused by the intermittent movement of the gas.

28. The apparatus of claim 26, wherein said optical conductor is an optical fiber, the sensing surface being an end surface of said optical conductor.

29. The apparatus of claim 26, wherein said optical conductor is an optical fiber, the sensing surface being a side surface of said optical fiber.

30. The apparatus of claim 26, further comprising means for attachment to a nostril, such that the apparatus may detect moisture in an air flow passing through the nostril of a man or animal.

* * * * *